(12) United States Patent
Slykerman et al.

(10) Patent No.: US 11,439,674 B2
(45) Date of Patent: Sep. 13, 2022

(54) USE OF LACTIC ACID BACTERIA TO TREAT OR PREVENT AT LEAST ONE OF POSTNATAL DEPRESSION AND POSTNATAL ANXIETY

(71) Applicant: UNIVERSITY OF OTAGO, Dunedin (NZ)

(72) Inventors: Rebecca Slykerman, Auckland (NZ); Edwin Arthur Mitchell, Auckland (NZ); Thorsten Villiers Stanley, Wellington (NZ)

(73) Assignee: University of Otago, Dunedin (NZ)

( * ) Notice: Subject to any disclaimer, the term of this patent is extended or adjusted under 35 U.S.C. 154(b) by 0 days.

(21) Appl. No.: 16/617,813

(22) PCT Filed: Jun. 2, 2017

(86) PCT No.: PCT/IB2017/053263
§ 371 (c)(1),
(2) Date: Nov. 27, 2019

(87) PCT Pub. No.: WO2018/220429
PCT Pub. Date: Dec. 6, 2018

(65) Prior Publication Data
US 2020/0188454 A1 Jun. 18, 2020

(51) Int. Cl.
| | | |
|---|---|---|
| *A61K 35/747* | (2015.01) |
| *A23C 9/123* | (2006.01) |
| *A23L 33/21* | (2016.01) |
| *A23L 33/135* | (2016.01) |
| *A23L 33/00* | (2016.01) |
| *A61P 25/22* | (2006.01) |
| *A61P 25/24* | (2006.01) |
| *C12N 1/20* | (2006.01) |
| *C12R 1/225* | (2006.01) |

(52) U.S. Cl.
CPC .......... *A61K 35/747* (2013.01); *A23L 33/135* (2016.08); *A23L 33/21* (2016.08); *A23L 33/40* (2016.08); *A61P 25/22* (2018.01); *A61P 25/24* (2018.01); *C12N 1/205* (2021.05); *A23V 2002/00* (2013.01); *A23Y 2220/73* (2013.01); *C12R 2001/225* (2021.05)

(58) Field of Classification Search
CPC .. A61K 35/747; A23L 33/135; A23Y 2220/73
See application file for complete search history.

(56) References Cited

U.S. PATENT DOCUMENTS

| | | | |
|---|---|---|---|
| 2011/0077044 A1 | 7/2011 | Thomas et al. | |
| 2011/0177044 A1 | 7/2011 | Thomas et al. | |
| 2017/0312232 A1* | 11/2017 | Vitetta | A61P 25/22 |

FOREIGN PATENT DOCUMENTS

| | | |
|---|---|---|
| CN | 101791125 | 8/2010 |
| CN | 102994432 A | 3/2013 |
| RU | 2208632 | 7/2003 |
| WO | WO 1999/010476 | 3/1999 |
| WO | WO 2010/060722 | 6/2010 |
| WO | WO 2010/064930 | 6/2010 |
| WO | WO 2016/198528 | 12/2016 |

OTHER PUBLICATIONS

Tendais et al, "Screening for Depression and Anxiety Disorders from Pregnancy to Pospartum with EPDS and STAI" Spanish Journal of Psychology (2014) 17, p. 1-9 (Year: 2014).*
Ceapa et al, The variable regions of Lactobacillus rhamnosus genomes reveal the dynamic evolution of metabolic and host-adaptation repertoires, Genome Biol. Evol. 8(6): 1889-1905 (Year: 2016).*
Toscano et al, "Effect of Lactobacillus rhamnosus HN001 and Bifidobacterium longum BB536 on the healthy gut microbiota composition at phyla and species level: a preliminary study," World J. Gastroenterology, Apr. 21, 2017: 23(15): 2696-2704 (Year: 2017).*
National Health Society, Entry on Overview of Postnatal Depression, https://www.nhs.uk/conditions/post-natal-depression/, accessed on Nov. 6, 2020 for evidentiary purposes only (Year: 2020).*
Dennis, Cindy-Lee, "Psychosocial and psychological interventions for prevention of postnatal depression: systematic review," BMJ Papers vol. 331, Jul. 2, 2005, p. 1-8 (Year: 2005).*
Barthow, C. et al. "The Probiotics in Pregnancy Study (PiP Study): rationale and design of a doubleblind randomised controlled trial to improve maternal health during pregnancy and prevent infant eczema and allergy" BMC Pregnancy and Childbirth (Jun. 3, 2016) vol. 16 No. 133, p. I to 14 Abstract, "Maternal postpartum depression and anxiety and probiotics" pp. 4 to 5.
Karadag, N. et al. "Treatment of infantile colic with lactobacillus reuteri and the relationship with postpartum depression: A randomized controlled trial study" Archives of Disease in Childhood (2012) vol. 97 Suppl.2, Abstract 1678, pages A474 to A475, whole document.
International Search Report and Written Opinion in PCT/IB2017/053263 dated Aug. 18, 2017 in 10 pages.
Barthow et al., "The Probiotics in Pregnancy Study (PiP Study): rationale and design of a doubleblind randomised controlled trial to improve maternal health during pregnancy and prevent infant eczema and allergy", BMC Pregnancy and Childbirth (Jun. 3, 2016) vol. 16 No. 133, pp. 1-14.

(Continued)

*Primary Examiner* — Michelle F. Paguio Frising
(74) *Attorney, Agent, or Firm* — Knobbe, Martens, Olson & Bear, LLP

(57) ABSTRACT

The present invention provides methods of treating or preventing at least one of postnatal depression (PND) and postnatal anxiety (PNA), and risks and sequelae thereof, by administering *Lactobacillus rhamnosus* HN001 or derivatives thereof, in addition to uses, compositions, and medicaments comprising *Lactobacillus rhamnosus* HN001 or derivatives thereof to treat or prevent at least one of PND and PNA, and risks and sequelae thereof.

22 Claims, 1 Drawing Sheet

(56) References Cited

OTHER PUBLICATIONS

Karadag et al., "Treatment of infantile colic with lactobacillus reuteri and the relationship with postpartum depression: A randomized controlled trial study", Archives of Disease in Childhood (2012) vol. 97, Suppl. 2, Abstract 1678, pp. A474-A475.

Abbott et al., "Postnatal depressive symptoms among Pacific mothers in Auckland: prevalence and risk factors", 2006, Aust N Z J Psychiatry, vol. 40, pp. 230-238.

PMMRC "Eighth annual report of the Perinatal and Maternal Mortality Review Committee: Reporting mortality 2012", Jun. 2014, Health Quality & Safety Commission New Zealand.

Da Costa et al., "Health-related quality of life in postpartum depressed women", Arch Women's Ment Health, 2006, vol. 9, pp. 95-102.

Tronick et al., "Infants of Depressed Mothers", Apr. 2009, Harvard Rev Psychiatry, vol. 17, pp. 147-156.

Grace et al., "The effect of postpartum depression on child cognitive development and behavior: a review and critical analysis of the literature", 2003, Arch Women's Ment Health, vol. 6, pp. 263-274.

Battle CL, Salisbury AL, Schofield CA, Ortiz-Hernandez S (2013): Perinatal antidepressant use: understanding women's preferences and concerns J Psychiatr Pract 19: 443-53.

Dinan TG, Cryan JF (2016): Mood by microbes: towards clinical translation. Genome Med 6:36-38.

Collins SM, Kassam Z, Bercik P (2013): The adoptive transfer of behavioral phenotype via the intestinal microbiota: experimental evidence and clinical implications. Curr Opin Microbiol 16: 240-5.

Bravo JA, Forsythe P, Chew MV, Escaravage E, Savignac HM, Dinan TG, et al. (2011): Ingestion of Lactobacillus strain regulates emotional behaviour and central GABA receptor expression in a mouse via the vagus nerve. PNAS 108: 16050-16059.

Desbonnet L, Garrett L, Clarke G, Kiely B, Cryan JF, Dinan TG (2010): Effect of the probiotic Bifidobacterium Infantis in the maternal separation model of depression. Neuroscience 170: 1179-1188.

Carabotti M, Scirocco A, Maselli MA, Severi C (2015): The gut-brain axis: interactions between enteric microbiota, central and enteric nervous systems. Ann Gastroenterol 28: 203-209.

Romijn AR, & Rucklidge, JJ (2015): Systematic review of evidence to support the theory of psychobiotics. Nutr Rev 73: 675-693.

Cox JL, Holden J M & Sagovsky R (1987): Detection of postnatal depression. Development of the 10-item Edinburgh Postnatal Depression Scale. Br J Psychiatry 150: 782-786.

Marteau TM, Bekker H (1992): The development of a six-item short-form of the state scale of the Spielberger State-Trait Anxiety Inventory (STAI). Br J Clin Psychol 31: 301-6.

Akkasheh G, Kashani-Poor Z, Tajabadi-Ebrahimi M, Jafari P, Akbari H, Taghizadeh M, et al. (2016): Clinical and metabolic response to probiotic administration in patients with major depressive disorder: A randomized, double-blind, placebo-controlled trial. Nutrition 32: 315-320.

Rao AV, Bested AC, Beaulne TM, Katzman MA, Iorio C, Beradi JM, et al. (2009): A randomized, double-blind, placebo-controlled pilot study of a probiotic in emotional symptoms of chronic fatigue syndrome. Gut Pathog. 1:1-6.

Dickerson FB, Stallings C, Origoni A, Katsafanas E, Savage CL, Schweinfurth LA, et al. (2014): Effects of probiotic supplementation on schizophrenia symptoms and association with gastrointestinal functioning: A randomised, placebo-controlled trial. Prim Care Companion CNS Disord 16. pii: PCC.13m01579.

Reale M, Boscolo P, Bellante V, Tarantelli C, Di Nicola M, Forcella L, et al. (2012): Daily intake of Lactobacillus casei Shirota increases natural killer cell activity in smokers. Br J Nutr 108: 308-314.

Dapoigny M, Piche T, Ducrote P, Lundard B, Cardot J, Bernalier-Donadille A (2012): Efficacy and safety profile of LCR35 complete freeze-dried culture in irritable bowel syndrome: a randomized double-blind study. World J Gastroenterol 18: 2067-2075.

Mi G, Zhao L, Qiao D, Kang W, Tang M, & Xu J (2015): Effectiveness of Lactobacillus reuteri in infantile colic and colicky induced maternal depression: A prospective single blind randomized trial. Antonie van Leeuwenhoek 107: 154-155.

Craig M, and Howard, L (2009): Postnatal depression, BMJ Clin Evid, Published online Jan. 26, 2009.

Jiang H, Ling Z, Zhang Y, Mao H, Ma Z, Yin Y, et al. (2015): Altered fecal microbiota composition in patients with major depressive disorder. Brain Behav Immun 48: 186-194.

Sung V, Hiscock H, Tang M, Mensah F, Nation M, Satzke C, et al. (2014): Treating infant colic with the probiotic Lactobacillus reuteri: double blind placebo controlled randomised trial. BMJ 348: 2107.

Aaltonen, J, Ojala, T, Laitinen, K, Poussa, T, Ozanne, S, Isolauri, E (2011): Impact of maternal diet during pregnancy and breastfeeding on infant metabolic programming: a prospective randomized controlled study. European Journal of Clinical Nutrition 65: 10-19.

Food and Agriculture Organization/World Health Organization (2002) Guidelines for the evaluation of probiotics in food. Report of a joint FAO/WHO Working Group on drafting guidelines for the evaluation of probiotics in food. Ontario, Canada.

Gomes AC, Beuno AA, de Souza RGM , Mota JF (2014) Gut microbiota, probiotics and diabetes. Nutr J 1310.1186/1475-2891-13-60.

Zhang Q, Yucheng W, Xiaoqiang F (2016) Effect of probiotics on glucose metabolism in patients with type 2 diabetes mellitus; A meta-analysis of randomized controlled trials. Medicina 52: 28-34.

Thomas LV, Ockhuizen T, Suzuki K (2014) Exploring the influence of the gut microbiota and probiotics on health: a symposium report. Br J Nutr 112: S1-S18. doi:10.1017/S0007114514001275.

Wickens K, Black PN, Stanley TV, et al. (2008) A differential effect of 2 probiotics in the prevention of eczema and atopy: A double-blind, randomized, placebo-controlled trial. J Allergy Clin Imunol 122: 788-794.

Laitinen K, Poussa T, Isolauri E, and the Nutrition, Allergy, Mucosal Immunology and Intestinal Microbiotia Group (2009) Probiotics and dietary counselling contribute to glucose regulation during and after pregnancy: a randomized controlled trial. Br J Nutr 101: 1679-1687.

Lindsay KL, Kennelly M, Culliton M, et al. (2014) Probiotics in obese pregnancy do not reduce maternal fasting glucose: a double-blind, placebo-controlled, randomized trial (Probiotics in Pregnancy Study). Am J Clin Nutr 99:1432-1439.

Lindsay KL, Brennan L, Kennelly MA, et al. (2015) Impact of probiotics in women with gestational diabetes mellitus on metabolic health: a randomized controlled trial. Am J Obstet Gynecol 212: 496.e491.

Francino MP (2016) Antibiotics and the human gut microbiome: dysbiosis and accumulation of resistances. Front Microbiol 6:1543. 10.3389/fmicb.2015.01543.

Koren O, Goodrich JK, Tyler CC, et al. (2012) Host remodelling of the gut microbiome and metabolic changes during pregnancy. Cell 150: 470-480.

Prescott SL (2013) Early-life environmental determinants of allergic diseases and the wider pandemic of inflammatory noncommunicable diseases. J Allergy Clin Immunol 131: 23-30.

Barrett, HL, et al. "Probiotics for preventing gestational diabetes (Review)" Cochrane Database of Systematic Reviews (2014), Issue 2. Article No. CD009951 [online], <URL: http://onlinelibrary.wiley.com/doi/10.1002/14651858.CD009951.pub2/full>.

Nitert MD, Barrett HL, Foxcroft K, Tremellen A, Wilkinson S, Lingwood B, et al. SPRING: an RCT study of probiotics in the prevention of gestational diabetes mellitus in overweight and obese women. BMC Pregnancy Childbirth. 2013; 13:50.

Logan Alan C et al. "Major depressive disorder: probiotics may be an adjuvant therapy", Medical Hypotheses, Eden Press, Penrith, US, vol. 64, No. 3, Jan. 1, 2005, pp. 533-538, XP002534278.

Zheng, J., Wittouch, S., Salvetti, E. Franz, C. M. A. P., Harris, H. M. B., Mattarelli, P., O'Toole P. W., Pot, B., Vandamme, P., walter, J., Watanabe, K., Wuyts, S., Felis, G. E., Ganzle, M. G., Lebeer, S. A taxonomic note on the genus *Lactobacillus*: Description of 23 novel genera, emended description of the genus *Lactobacillus* Beijerinck 1901, and union of Lactobacillaceae and Leuconostocaceae. Int. J. Syst. Evol. 2020. 70. 2782-2858.

(56) References Cited

OTHER PUBLICATIONS

Luoto R, Laitinen K, Nermes M, Isolauri E (2010) Impact of maternal probiotic-supplemented dietary counselling on pregnancy outcome and prenatal and postnatal growth: a double-blind, placebo-controlled study. Br J Nutr 103: 1792-1799.

Murray et al., "Effects of postnatal depression on infant development", Arch Dis Child, 1997, pp. 99-101.

Luoto et al., "Impact of maternal probiotic-supplemented dietary counseling during pregnancy on colostrum adiponectin concentration: A prospective, randomized, placebo-controlled study", Early Human Development, 2012, vol. 88, pp. 339-344.

Bharwani et al., "Oral treatment with Lactobacillus rhamnosus attenuates behavioural deficits and immune changes in chronic social stress", BMC Medicine, 2017, vol. 15, No. 7, 14 pages.

Kantak et al., "Obsessive-compulsive-like behaviors in house mice are attenuated by a probiotic (Lactobacillus rhamnosus GG)", Behavioural Pharmacology, 2014, vol. 25, pp. 71-79.

Janik et al., "Magnetic resonance spectroscopy reveals oral Lactobacillus promotion of increases in brain GABA, N-acetyl aspartate and glutamate", NeuroImage, 2016, vol. 125, pp. 988-995.

Kelly et al., "Lost in translation? The potential psychobiotic Lactobacillus rhamnosus (JB-1) fails to modulate stress or cognitive performance in healthy male subjects", Brain, Behavior, and Immunity, 2016, 10 pages.

Reis et al., "The anxiolytic effect of probiotics: A systematic review and meta-analysis of the clinical and preclinical literature", PLoS One, Jun. 20, 2018, vol. 13, No. 6, 25 pages, htttps://doi.org/10.1371/journal.pone.0199041.

Slykerman et al., "Effect of Lactobacillus rhamnosus HN001 in Pregnancy on Postpartum Symptoms of Depression and Anxiety: A Randomised Double-blind Placebo-controlled Trial", EBioMedicine, 2017, vol. 24, pp. 159-165.

Romijn et al., "A double-blind, randomized, placebo-controlled trial of Lactobacillus helveticus and Bifidobacterium longum for the symptoms of depression", Australian & New Zealand Journal of Psychiatry, 2017, vol. 51, No. 8, pp. 810-821.

Anzctr, "PiP trial registration: A maternal probiotic intervention for infant allergic disease prevention", Feb. 2012, pp. 1-8.

\* cited by examiner

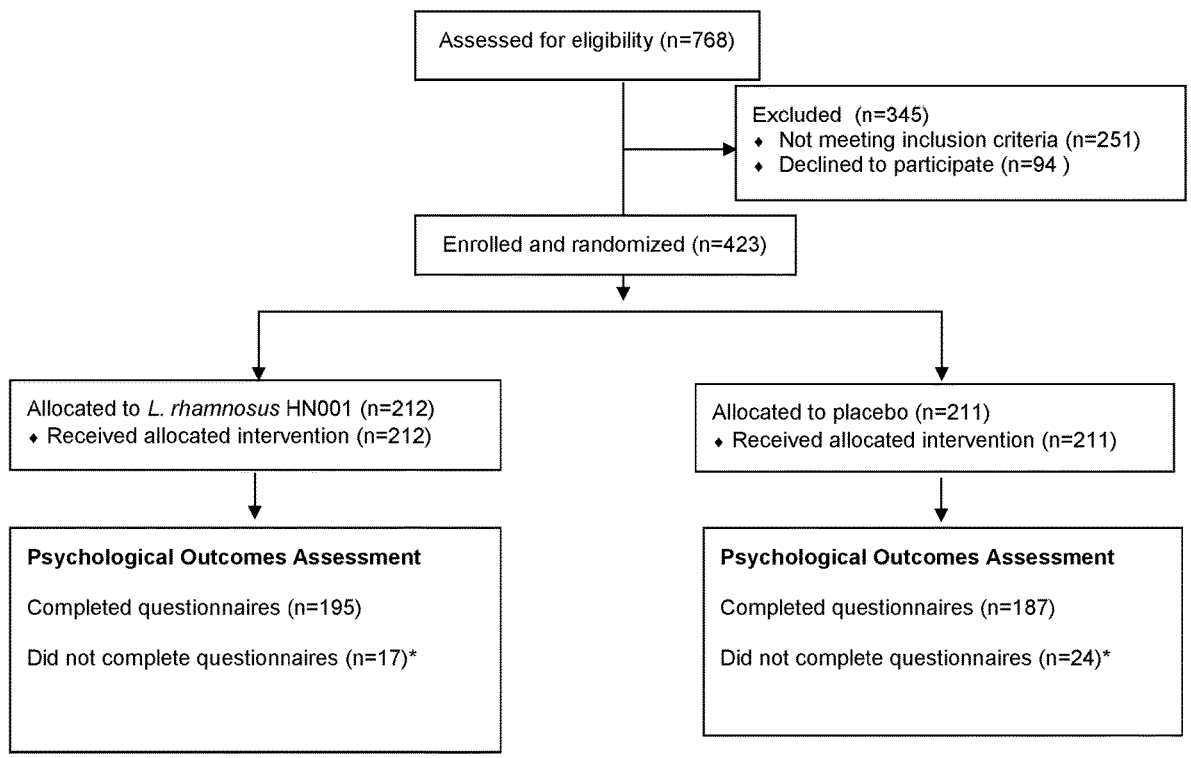

USE OF LACTIC ACID BACTERIA TO TREAT OR PREVENT AT LEAST ONE OF POSTNATAL DEPRESSION AND POSTNATAL ANXIETY

REFERENCE TO RELATED APPLICATIONS

This application is the U.S. National Phase of International Application PCT/IB2017/053263, which is incorporated by reference herein. Any and all applications for which a foreign or domestic priority claim is identified in the Application Data Sheet as filed with the present application are hereby incorporated by reference under 37 C.F.R. § 1.57.

TECHNICAL FIELD

This invention relates to the use of probiotic bacteria and in particular the use of a strain of lactic acid bacteria to treat and/or prevent at least one of postnatal depression (PND) and postnatal anxiety (PNA). Methods for using the bacteria and compositions comprising the bacteria are also provided.

BACKGROUND

Major depression in pregnancy and after birth occurs in 10-15% of women in New Zealand a rate comparable to other western countries (1). Postnatal depression (PND) is associated with persistent depression, and even, in a few cases each year, death from suicide (2). This disorder may affect a mothers' ability to care for, and bond with, her new infant as well are her quality of life and daily functioning (3). In addition, maternal depression can produce long-lasting effects on children's cognitive, social-emotional and health outcomes (4, 5). Safe and effective therapies to prevent and treat PND are needed (6).

Increasingly, literature linking the health of the microbiota in the gut to brain chemistry and behaviour via multiple bi-directional pathways, including the immune system, hypothalamic pituitary adrenal axis (HPA axis) and a vast network of afferent and efferent nerves linking the gut to the central nervous system, suggest that probiotic enhancement of gut microbiota may improve mood outcomes (7).

Pre-clinical studies have demonstrated that the anxiety phenotype of mice can be changed with faecal transplantation and that the changes in microbiota are accompanied by changes in brain chemistry (8). Furthermore, probiotic treatment has also been shown to have a positive effect on anxiety-like and depressive-like behaviour in animal studies (9, 10) with mediating mechanisms including GABA receptor expression in specific locations of the central nervous system (9), the HPA axis (10) and the vagus nerve which transmits information from the gut luminal environment to the CNS (11). Clinical trials of probiotic treatment have yielded mixed results and a recent systematic review of human trials concluded that the evidence for beneficial effects of probiotics on mood may not be as strong as some recent narrative studies have purported. They suggest further randomised controlled trials (RCT) are needed (12).

Current treatment or prevention of PND and postnatal anxiety is generally based on pharmacology and psychotherapy. However, many women are concerned that there is a lack of strong evidence evaluating the safety of depression drugs that are passed into breast milk. Furthermore, for some women there is a stigma attached to seeking psychological treatment.

Antidepressants are often one of the first lines of therapy against PND and postnatal anxiety. Conventional antidepressants such as tricyclics and selective serotonin reuptake inhibitors (SSRIs) are commonly prescribed. However, there are many problems associated with the use of these conventional antidepressants for PND. First, these conventional antidepressants typically alleviate the PND condition in no more than about 80% of the patients taking them. Second, even when successful, these conventional antidepressants typically take up to 8 weeks be effective. Third, the mother can expect to experience the typical side effects associated with tricyclics and SSRIs. Side effects associated with tricyclics use include dry mouth, dry nose, blurred vision, decreased gastro-intestinal motility and secretion. Anti-depressant use can also result in drowsiness, irritability, and poor-feeding in nursing mothers. Fourth, in rare cases, treatment with antidepressants can lead to worsening of PND or postnatal anxiety symptoms, or to the development of mania or psychosis. While psychotherapy can be as effective as antidepressants in treating PND and postnatal anxiety, interventions tend to be available for limited time periods (e.g. 10 to 20 weeks), require specialist service providers that may not be available in all areas, and the long-term benefits remain unclear (22).

Thus there remains a need for methods and compositions useful to treat and/or prevent PND and PNA, and particularly methods and compositions for treating or preventing PND and PNA which do not rely on either prescription drug and/or counseling. Methods and compositions for the prevention or amelioration of PND and PNA also desirable.

It is an object of this invention to go some way towards achieving one or more of these desired data or at least to offer the public a useful choice.

SUMMARY OF THE INVENTION

In a first aspect the invention provides a method of treating or preventing of at least one of postnatal depression (PND) and postnatal anxiety (PNA) in a subject, the method comprising administration of *Lactobacillus rhamnosus* HN001, AGAL deposit number NM97/09514 dated 18 Aug. 1997 to a subject in need thereof.

In one embodiment, the *L. rhamnosus* HN001 is administered in the form of a composition with a physiologically acceptable diluent, adjuvant, carrier or excipient.

In one embodiment, HN001 is the only probiotic bacteria administered.

In one embodiment, HN001 is administered with one or more prebiotics.

In one embodiment, said physiologically acceptable diluent, adjuvant, carrier or excipient is a food. In one embodiment, the food is cultured milk, yoghurt, cheese, milk drink or milk powder.

Alternatively the composition is a pharmaceutical composition and said excipient or diluent is pharmaceutically acceptable diluent, adjuvant, carrier or excipient.

In another aspect the invention provides a method of treating or preventing one or more risk associated with at least one of PND or PNA, wherein the risk is to an infant born, or to be born to a subject, the method comprising administration of *Lactobacillus rhamnosus* HN001, AGAL deposit number NM97/09514 dated 18 Aug. 1997 to the subject in need thereof.

In one embodiment, the composition is a maternal formula or a maternal supplement.

The composition may be a formula, for example a maternal formula, dietetic product, and hypoallergenic embodiments thereof.

In preferred embodiments, the method comprises administering a composition comprising L. rhamnosus HN001 to the subject. Preferably, the composition is a supplement, formula, dietetic product or food.

In certain embodiments, the L. rhamnosus HN001 is in a reproductively viable form, preferably in a reproductively viable form and amount. In other embodiments, the L. rhamnosus HN001 is killed, lysed, fractionated or attenuated.

The invention further provides L. rhamnosus HN001 for treating or preventing at least one of PND or PNA, or for treating or preventing one or more risk associated with, or one or more sequelae of, at least one of PND or PNA The invention further provides L. rhamnosus HN001 in the manufacture of a composition for treating or preventing at least one of PND or PNA or for treating or preventing one or more risk associated with, or one or more sequelae of, at least one of PND or PNA. The composition may be a composition such as those as described herein including, for example, a food or medicament.

It will be appreciated that the invention also contemplates the use of L. rhamnosus HN001 in the manufacture of a composition of the invention, for example a composition for treating or preventing at least one of PND or PNA in a subject.

In one embodiment the composition is suitable for oral administration. In other embodiments, the composition is suitable for parenteral administration. In embodiments relating to preventing one or more risk associated with, or one or more sequelae of, at least one of PND or PNA in a foetal subject, the composition is suitable for oral administration to a pregnant mother during gestation.

In various embodiments, the method is a method of treating or preventing at least one of PND or PNA in a subject having an increased risk of at least one of PND or PNA. In one embodiment, the method is a method of treating or preventing at least one of PND or PNA in a subject who has previously suffered at least one of PND or PNA.

In a further embodiment the subject has suffered from, experienced, has or had, one or more of: prenatal depression or anxiety, a personal or family history of depression, moderate to severe premenstrual symptoms, maternity blues, birth-related psychological trauma, birth-related physical trauma, previous stillbirth or miscarriage, cigarette smoking, low self-esteem, childcare or life stress, low social support, poor marital relationship or single marital status, and low socioeconomic status.

In one embodiment, the method is a method of preventing recurrence of at least one of PND or PNA in a subject who has previously suffered from at least one of PND or PNA, the method comprising administering an effective amount of HN001 or a derivative thereof to a subject in need thereof.

In one embodiment, the method comprises beginning administration of HN001 after the first trimester of pregnancy. In one embodiment, administration of HN001 begins between 14-16 weeks gestation.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

FIG. 1 shows the number eligible, recruited and allocated in the PIP Study described in the Example section. *women did not complete the psychological outcomes questionnaire for various reasons including: pregnancy complications, maternal ill health, preterm birth, refusal and could not be contacted.

DETAILED DESCRIPTION OF THE INVENTION

The present invention recognises for the first time the beneficial effects of administration of the lactic acid bacteria L. rhamnosus HN001 on the incidence and severity of at least one of PND or PNA.

Accordingly, in a first aspect the invention provides a method of treating or preventing at least one of PND or PNA in a subject, the method comprising administration of Lactobacillus rhamnosus HN001, AGAL deposit number NM97/09514 dated 18 Aug. 1997 or a derivative thereof to a subject in need thereof.

In a further aspect, the invention also provides a method of treating or preventing one or more risk associated with, or one or more sequelae of, at least one of PND and PNA in a subject, the method comprising administration of Lactobacillus rhamnosus HN001 or a derivative thereof to a subject in need thereof.

In a preferred embodiment the method treats or prevents both PND and PNA or an associated risk or sequelae thereof.

Symptoms associated with at least one of PND in a subject include, for example but not limited to: sadness, hopelessness, crying episodes, low self-esteem, irritability, guilt, a feeling of being overwhelmed, changes in sleeping patterns, changes in eating patterns, inability to be comforted, exhaustion, emptiness, inability to experience pleasure from activities usually found enjoyable, social withdrawal, low or no energy, becoming easily frustrated, feeling inadequate in taking care of the baby, decreased sex drive, occasional or frequent anxiety, interference with normal maternal-infant bonding.

Symptoms associated with at least one of PNA in a subject include, for example but not limited to: feelings of fear and worry which begin to dominate thinking, feeling irritable, feeling restless, feeling tense, feeling 'on edge', racing heart/strong palpitations, panic attacks, reoccurring worrying thoughts, feeling out of control, feeling that you are not doing things right, feeling that something terrible will happen, insomnia, avoiding situations for fear something bad will happen.

Risks associated with, and sequelae of, at least one of PND and PNA in a foetal, neonatal, infant, child or adult subject (in particular, subjects whose birth mother suffered from at least one of PND and PNA) include for example, but not limited to: higher rates of emotional problems, behavioural problems, psychiatric diagnoses (such as oppositional defiant disorder and conduct disorder), and hyperactivity.

While various routes and methods of administration are contemplated, oral administration of *L. rhamnosus* HN001, such as in a composition suitable for oral administration, is currently preferred. It will of course be appreciated that other routes and methods of administration may be utilised or preferred in certain circumstances. For example, a parenteral route may be utilised with a composition comprising killed or attenuated *L. rhamnosus* HN001 or a derivative thereof.

The term "oral administration" includes oral, buccal, enteral and intra-gastric administration.

The term "parenteral administration" includes but is not limited to topical (including administration to any dermal, epidermal or mucosal surface), subcutaneous, intravenous, intraperitoneal, and intramuscular administration.

A "subject" is an animal, preferably a mammal, more preferably a mammalian companion animal or human. Preferred companion animals include cats, dogs and horses. In one embodiment the human is an adult, preferably a female adult, more preferably a pregnant female adult.

In a further embodiment, the subject intends to breastfeed her child when born. In a further embodiment, the subject is currently breastfeeding her child.

In one embodiment the father of the unborn, or born child, has a history of at least one of asthma, hayfever and eczema. In a further embodiment the at least one of asthma, hayfever and eczema required medication.

The term "treat" and its derivatives should be interpreted in their broadest possible context. The term should not be taken to imply that a subject is treated until total recovery. Accordingly, "treat" broadly includes amelioration and/or prevention of the onset at least one of the symptoms of, or the severity of a particular condition.

In one embodiment the treatment or prevention of PND results in a score of less than 13, preferably less than 12, more preferably less than 11, more preferably less than 10, more preferably less than 9, more preferably less than 8, more preferably less than 7, more preferably less than 6, more preferably less than 5, more preferably less than 4, more preferably less than 3, more preferably less than 2, more preferably less than 1 in the Edinburgh Postnatal Depression Scale (EPDS) screening questionnaire widely used to assess risk of postnatal depression (14).

In a further embodiment the treatment or prevention of PND results in a score of less than 15, preferably less than 14, more preferably less than 13, more preferably less than 12, more preferably less than 11, more preferably less than 10, more preferably less than 9, more preferably less than 8, more preferably less than 7, more preferably less than 6, more preferably less than 5, more preferably less than 4, more preferably less than 3, more preferably less than 2, more preferably less than 1 in the State Trait Anxiety Inventory 6 item version (STAI6) 6 item scale validated screening questionnaire screening questionnaire widely used to assess risk of anxiety (15).

State Trait Anxiety Inventory 6 item version (STAI6): The STAI6 is a short 6 item scale validated as an anxiety screening questionnaire based on the longer State Trait Anxiety Inventory (15). A cut-off of score >15 was used as an indicator of clinically significant levels of anxiety.

It will be appreciated that treatment includes prophylactic treatment, such as for example, the prophylactic treatment of a subject, such as a subject having an expected or established increased risk of at least one of PND or PNA and/or a subject attempting to become or recently pregnant, or the prophylactic treatment of one or more risk associated with, or one or more sequelae of, at least one of PND or PNA in a foetal subject by indirect administration of a composition of the invention by administering the composition to the foetal subject's mother.

In another example, the prophylactic treatment of one or more risk associated with, or one or more sequelae of, at least one of PND or PNA is of a neonatal, infant or child subject by indirect administration of a composition of the invention by administering the composition to the subject's breastfeeding mother.

It will be further appreciated that treatment includes therapeutic treatment, such as for example, treatment of at least one of PND and PNA or one or more symptoms of or risks associated with at least one of PND and PNA, including for example the treatment of an neonatal, infant or child subject by indirect administration of a composition of the invention by administering the composition to the subject's mother.

Accordingly, the invention provides for a method of treating or preventing at least one of PND and PNA in a pregnant subject, the method comprising administration of *L. rhamnosus* HN001 or a composition comprising *L. rhamnosus* HN001 to the pregnant subject.

In certain embodiments, the pregnant subject is 35 years or older.

In certain embodiments, the pregnant subject has a history of at least one of PND and PNA.

In certain embodiments, the *L. rhamnosus* HN001 or a composition comprising *L. rhamnosus* HN001 is administered from 14 to 16 weeks gestation until delivery.

In certain embodiments, the *L. rhamnosus* HN001 or a composition comprising *L. rhamnosus* HN001 is administered from 14 to 16 weeks gestation to 6 months postpartum.

Accordingly, the invention provides a method of preventing one or more risk associated with, or one or more sequelae of, at least one of PND or PNA in a foetal subject, the method comprising administration of *L. rhamnosus* HN001 or a composition comprising *L. rhamnosus* HN001 to the subject's mother.

Also provided is a method of treating or preventing one or more risk associated with, or one or more sequelae of, at least one of PND or PNA in a neonatal, infant, or child subject, the method comprises administering *L. rhamnosus* HN001 or a composition comprising *L. rhamnosus* HN001 to the subject's mother.

A method of treating one or more risk associated with, or one or more sequelae of, at least one of PND or PNA in an infant or child subject comprising administering a composition consisting of or consisting essentially of *L. rhamnosus* HN001 is also contemplated.

In certain embodiments, the infant or child is considered to be at risk of one or more risk associated with, or one or more sequelae of, at least one of PND or PNA due to the prior incidence of at least one of PND or PNA in the infant or child's mother.

1 *Lactobacillus rhamnosus* HN001

As described in the applicant's PCT International application PCT/NZ98/00122 (published as WO 99/10476 and incorporated herein in its entirety), a freeze-dried culture of *Lactobacillus rhamnosus* HN001 was deposited at the Australian Government Analytical Laboratories (AGAL), The New South Wales Regional Laboratory, 1 Suakin Street, Pymble, NSW 2073, Australia, on 18 Aug. 1997 and was accorded deposit number NM97/09514. This Budapest Treaty-recognised depository is now no longer referred to as AGAL, but rather is referred to as the National Measurement Institute of Australia (NMIA). The genome sequence of *L. rhamnosus* HN001 is available at Genebank under accession number: NZ_ABWJ00000000.

1.1 Morphological Properties

The morphological properties of *L. rhamnosus* HN001 are described below.

Short to medium rods with square ends in chains, generally 0.7×1.1×2.0-4.0 µm, when grown in MRS broth.

Gram positive, non-mobile, non-spore forming, catalase negative facultative anaerobic rods with optimum growth temperature of 37±1° C. and optimum pH of 6.0-6.5. These are facultatively heterofermentative bacteria and no gas is produced from glucose.

1.2 Fermentative Properties

An API 50 CH sugar fermentation kit was used to determine the carbohydrate fermentation pattern of *L. rhamnosus* HN001, yielding a score of 5757177 (based on scores of 22 prominent sugars—see PCT/NZ98/00122).

1.3 Further Characterisation

*L. rhamnosus* strain HN001 may be further characterised by the functional attributes disclosed in PCT/NZ98/00122, including its ability to adhere to human intestinal epithelial cells, and by the improvements in phagocyte function, in antibody responses, in natural killer cell activity, and in lymphocyte proliferation elicited by dietary intake or in in vitro model systems. It will be appreciated that there are a wide variety of methods known and available to the skilled artisan that can be used to confirm the identity of *L. rhamnosus* HN001, wherein exemplary methods include DNA fingerprinting, genomic analysis, sequencing, and related genomic and proteomic techniques.

As described herein, certain embodiments of the present invention utilise live *L. rhamnosus* HN001. In other embodiments, a *L. rhamnosus* HN001 derivative is utilised.

As used herein, the term "derivative" and grammatical equivalents thereof when used with reference to bacteria (including use with reference to a specific strain of bacteria such as *L. rhamnosus* HN001) contemplates mutants and homologues of or derived from the bacteria, killed or attenuated bacteria such as but not limited to heat-killed, lysed, fractionated, pressure-killed, irradiated, and UV- or light-treated bacteria, and material derived from the bacteria including but not limited to bacterial cell wall compositions, bacterial cell lysates, lyophilised bacteria, probiotic factors from the bacteria, and the like, wherein the derivative retains probiotic activity. Methods to produce such derivatives, such as but not limited to one or more mutants of *L. rhamnosus* HN001 or one or more probiotic factors, and particularly derivatives suitable for administration to a subject (for example, in a composition) are well-known in the art.

It will be appreciated that methods suitable for identifying *L. rhamnosus* HN001, such as those described above, are similarly suitable for identifying derivatives of *L. rhamnosus* HN001, including for example mutants or homologues of *L. rhamnosus* HN001, or for example probiotic factors from *L. rhamnosus* HN001.

The term "probiotic factor" refers to a bacterial molecule responsible for mediating probiotic activity, including but not limited to bacterial DNA motifs, surface proteins, small organic acids, polysaccharides, or cell wall components such as lipoteichoic acids and peptidoglycan, or a mixture of any two or more thereof. While, as noted above, these molecules have not been clearly identified, and without wishing to be bound by any theory, such molecules will be present if a probiotic organism is present.

The term "probiotic activity" refers to the ability of certain microorganisms to stimulate the immune system. Measuring the type and level of activity of a probiotic microorganism is known to those skilled in the art; see, for example, Mercenier et al. (2004), Leyer et al. (2004), or Cummings et al. (2004). For example, probiotic activity may be assessed by a PBMC cytokine secretion assay.

Reference to retaining probiotic activity is intended to mean that a derivative of a probiotic microorganism, such as a mutant or homologue of a probiotic microorganism or an attenuated or killed probiotic microorganism still has useful probiotic activity, or that a composition comprising a probiotic microorganism or a derivative thereof is capable of supporting the maintenance of useful probiotic activity. While the bacterial molecules responsible for mediating probiotic activity have not been clearly identified, molecules that have been proposed as possible candidates include bacterial DNA motifs, surface proteins, small organic acids, polysaccharides, and cell wall components such as lipoteichoic acids and peptidoglycan. It has been postulated that these interact with components of the host immune system to give an immuno-modulatory effect. Preferably, the retained activity is at least about 35, 40, 45, 50, 55, 60, 65, 70, 75, 80, 85, 90, 95, 99 or 100% of the activity of an untreated (i.e., live or non-attenuated) control, and useful ranges may be selected between any of these values (for example, from about 35 to about 100%, from about 50 to about 100%, from about 60 to about 100%, from about 70 to about 100%, from about 80 to about 100%, and from about 90 to about 100%).

Using conventional solid substrate and liquid fermentation technologies well known in the art, *L. rhamnosus* HN001 can be grown in sufficient amounts to allow use as contemplated herein. For example, *L. rhamnosus* HN001 can be produced in bulk for formulation using nutrient film or submerged culture growing techniques, for example under conditions as described in WO99/10476. Briefly, growth is effected under aerobic conditions at any temperature satisfactory for growth of the organism. For example, for *L. rhamnosus* HN001 a temperature range of from 30 to 40° C., preferably 37° C., is preferred. The pH of the growth medium is slightly acidic, preferably about 6.0 to 6.5. Incubation time is sufficient for the isolate to reach a stationary growth phase.

*L. rhamnosus* HN001 cells may be harvested by methods well known in the art, for example, by conventional filtering or sedimentary methodologies (eg. centrifugation) or harvested dry using a cyclone system. *L. rhamnosus* HN001 cells can be used immediately or stored, preferably freeze-dried or chilled at −20° to 6° C., preferably −4° C., for as long as required using standard techniques.

2 Compositions

A composition useful herein may be formulated as a food, drink, food additive, drink additive, dietary supplement, nutritional product, medical food, enteral or parenteral feeding product, meal replacement, cosmeceutical, nutraceutical, or pharmaceutical. Appropriate formulations may be prepared by an art skilled worker with regard to that skill and the teaching of this specification.

In one embodiment, compositions useful herein include any edible consumer product which is able to carry bacteria or a bacterial derivative. Examples of suitable edible consumer products include powders, liquids, confectionary products including chocolate, gels, ice creams, reconstituted fruit products, snack bars, food bars, muesli bars, spreads, sauces, dips, dairy products including yoghurts and cheeses, drinks including dairy and non-dairy based drinks (such as milk drinks and yogurt drinks), milk powders, sports supplements including dairy and non-dairy based sports supplements, food additives such as protein sprinkles, dietary supplement products including daily supplement tablets, weaning foods and yoghurts, and formulas such as maternal formula, in powder or liquid form, including hypoallergenic embodiments of such compositions. Within this embodiment, a preferred composition useful herein may be a maternal formula, in powder or liquid form. Suitable nutraceutical compositions useful herein may be provided in similar forms.

Examples of formulas such as maternal formula, in powder or liquid form, include the following. It should be understood that the following formulations are indicative only and variations may be made according to known principles for formulating such products. For example, non-dairy sources of protein may be supplemented for the dairy proteins listed. Equally, hypoallergenic embodiments of these products may be provided where the protein source is fully or partially hydrolysed. Such hydrolysates are known in the art. One example of a maternal formula, useful herein comprises (w/w)

30-60% lactose
15-35% vegetable oils
0-40% skim milk powder
0-40% whey protein, such as a WPC or WPI, preferably an 80% WPC (WPC80)
0.001-50% of *L. rhamnosus* HN001.

Another example of a maternal formula, useful herein comprises (w/w)

40-60% lactose
20-30% vegetable oils
10-15% skim milk powder
6-8% whey protein, preferably WPC80
0.001-10% of *L. rhamnosus* HN001.

Another example of a maternal formula, herein comprises (w/w)

40-60% lactose
20-30% vegetable oils
10-15% skim milk powder
6-8% whey protein, preferably WPC80
0.001-5% of *L. rhamnosus* HN001.

Another example of a maternal formula, useful herein comprises (w/w)

40-60% lactose
20-30% vegetable oils
10-15% skim milk powder
6-8% whey protein, preferably WPC80
0.001-2% of *L. rhamnosus* HN001.

Any of these formulas may also comprise 0.1 to 4% w/w, preferably 2 to 4% w/w of one or more of a vitamin premix, a mineral premix, lecithin, one or more antioxidants, one or more stabilisers, or one or more nucleotides, or a combination of any two or more thereof. In some embodiments, these infant formulas may be formulated to provide between 2700 and 3000 kJ/L.

Examples of edible consumer products of the invention, such as dairy based drinks (such as milk drinks and yogurt drinks) will typically comprise and may consist of a protein source (such as a dairy protein source), a lipid source, a carbohydrate source, in addition to the *L. rhamnosus* HN001 or derivative thereof. Flavourants, colourants, and other additives, carriers or excipients as are well known to those skilled in the art may also be included.

A further example of an edible consumer product amenable to use in the present invention is the Unistraw™ delivery system (Unistraw International Limited, Australia) as described in PCT international application PCT/AU2007/000265 (published as WO 2007/098564) and PCT international application PCT/AU2007/001698 (published as WO 2008/055296), each incorporated herein in its entirety. It will be appreciated by those skilled in the art that *L. rhamnosus* HN001 and derivatives thereof, optionally together with one or more additional probiotic factor or probiotic agent, may be coated onto a substrate (for example, a water soluble bead) for use in such delivery systems.

In alternative embodiments, the compositions useful herein may be formulated to allow for administration to a subject by any chosen route, including but not limited to oral or parenteral (including topical, subcutaneous, intramuscular and intravenous) administration.

For example, a nutraceutical composition for use according to the invention can be a dietary supplement (e.g., a capsule, a mini-bag, or a tablet) or a food product (e.g., milk, juice, a soft drink, a herbal tea-bag, or confectionary). The composition can also include other nutrients, such as a protein, a carbohydrate, vitamins, minerals, or amino acids. The composition can be in a form suitable for oral use, such as a tablet, a hard or soft capsule, an aqueous or oil suspension, or a syrup; or in a form suitable for parenteral use, such as an aqueous propylene glycol solution, or a buffered aqueous solution. The amount of the active ingredient in the nutraceutical composition depends to a large extent on a subject's specific need. The amount also varies, as recognized by those skilled in the art, dependent on administration route, and possible co-usage of other probiotic factors or probiotic agents.

It will be appreciated that in certain embodiments, the compositions of the invention may be formulated so as to have a desired calorific content, for example so as to deliver a desired amount of energy or a desired percentage of daily recommended energy intake. For example, an edible consumer product may be formulated to provide from about 200 to about 2000 kJ per serve, or from about 500 kJ to about 2000 kJ per serve, or from about 1000 to about 2000 kJ per serve.

Thus, a pharmaceutical composition useful according to the invention may be formulated with an appropriate pharmaceutically acceptable carrier (including excipients, diluents, auxiliaries, and combinations thereof) selected with regard to the intended route of administration and standard pharmaceutical practice. For example, a composition useful according to the invention can be administered orally as a powder, liquid, tablet or capsule, or topically as an ointment, cream or lotion. Suitable formulations may contain additional agents as required, including emulsifying, antioxidant, flavouring or colouring agents, and may be adapted for immediate-, delayed-, modified-, sustained-, pulsed- or controlled-release.

The term "pharmaceutically acceptable carrier" is intended to refer to a carrier including but not limited to an excipient, diluent or auxiliary, pharmaceutically acceptable carrier includes a solvent, a dispersion medium, a coating, an antibacterial and antifungal agent, and an isotonic and absorption delaying agent or combination thereof, that can be administered to a subject as a component of a composition described herein that does not reduce the activity of the composition and is not toxic when administered in doses sufficient to deliver an effective amount of a compound or composition useful herein. The formulations can be administered orally, nasally or parenterally (including topically, intramuscularly, intraperitoneally, subcutaneously and intravenously).

In certain embodiments, a composition of the invention (such as, for example, a nutraceutical or pharmaceutical composition of the invention, may be provided as a capsule. Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Active ingredients can also be administered in a form of a hard shell tablet or a capsule containing a binder, e.g., lactose or mannitol, a conventional filler, and a tabletting agent. Pharmaceutical compositions can also be administered via the parenteral route. Examples of parenteral dosage forms include aqueous solutions, isotonic saline or 5% glucose of the active agent, or other well-known pharmaceutically acceptable excipients. Cyclodextrins, or other solubilising agents well-known to those familiar with the art, can be utilized as excipients for delivery of the therapeutic agent.

In certain embodiments, the composition of the invention comprises live *L. rhamnosus* HN001. Methods to produce such compositions are well-known in the art, and one such method is exemplified herein in the examples.

In other embodiments, the composition of the invention comprises one or more *L. rhamnosus* HN001 derivative. Again, methods to produce such compositions are well-known in the art, and may utilise standard microbiological and pharmaceutical practices.

It will be appreciated that a broad range of additives or carriers may be included in such compositions, for example to improve or preserve bacterial viability or to increase therapeutic efficacy of *L. rhamnosus* HN001 or of one or more *L. rhamnosus* HN001 derivatives. For example, additives such as surfactants, wetters, humectants, stickers, dispersal agents, stablisers, penetrants, and so-called stressing additives to improve bacterial cell vigor, growth, replication and survivability (such as potassium chloride, glycerol, sodium chloride and glucose), as well as cryoprotectants such as maltodextrin, may be included. Additives may also include compositions which assist in maintaining microorganism viability in long term storage, for example unrefined corn oil, or "invert" emulsions containing a mixture of oils and waxes on the outside and water, sodium alginate and bacteria on the inside.

In certain embodiments, the *L. rhamnosus* HN001 is in a reproductively viable form and amount.

The composition may comprise a carbohydrate source, such as a disaccharide including, for example, sucrose, fructose, glucose, or dextrose. Preferably the carbohydrate source is one able to be aerobically or anaerobically utilised by *L. rhamnosus* HN001.

In such embodiments, the composition preferably is capable of supporting reproductive viability of the *L. rhamnosus* HN001 for a period greater than about two weeks, preferably greater than about one month, about two months, about three months, about four months, about five months, more preferably greater than about six months, most preferably at least about 2 years to about 3 years or more.

In certain embodiments, the composition for treating or preventing at least one of PND or PNA, or one or more risk associated with, or one or more sequelae of, at least one of PND or PNA, comprises a probiotic comprising *L. rhamnosus* HN001 and a prebiotic, for example fructooligosaccharides, galactooligosaccharides, human milk oligosaccharides and combinations thereof.

In another embodiment, the method of treating and preventing at least one of PND or PNA, or one or more risk associated with, or one or more sequelae of, at least one of PND or PNA in a subject comprises administering an individual with an effective amount of a composition comprising *L. rhamnosus* HN001 and a prebiotic, for example fructooligosaccharides, galactooligosaccharides, human milk oligosaccharides and combinations thereof. In certain embodiments, an oral composition is formulated to allow the administration of a sufficient amount of *L. rhamnosus* HN001 to establish a population in the gastrointestinal tract of the subject when ingested. The established population may be a transient or permanent population.

In theory one colony forming unit (cfu) should be sufficient to establish a population of *L. rhamnosus* HN001 in a subject, but in actual situations a minimum number of units are required to do so. Therefore, for therapeutic mechanisms that are reliant on a viable, living population of probiotic bacteria, the number of units administered to a subject will affect therapeutic efficacy.

As presented herein in the examples, the Applicants have determined that a dosage rate of $6 \times 10^9$ cfu *L. rhamnosus* HN001 per day is sufficient (but may not be necessary) to establish a population in the gastrointestinal tract of human subjects. Accordingly, in one example, a composition formulated for administration will be sufficient to provide at least about $6 \times 10^9$ cfu *L. rhamnosus* HN001 per day.

Methods to determine the presence of a population of gut flora, such as *L. rhamnosus* HN001, in the gastrointestinal tract of a subject are well known in the art, and examples of such methods are presented herein. In certain embodiments, presence of a population of *L. rhamnosus* HN001 can be determined directly, for example by analysing one or more samples obtained from a subject, and determining the presence or amount of *L. rhamnosus* HN001 in said sample. In other embodiments, presence of a population of *L. rhamnosus* HN001 can be determined indirectly, for example by observing a reduction in symptoms of at least one of PND and PNA, or a decrease in the number of other gut flora in a sample obtained from a subject. Combinations of such methods are also envisaged.

The efficacy of a composition useful according to the invention can be evaluated both in vitro and in vivo. See, for example, the examples below. Briefly, the composition can be tested for its ability to prevent or treat at least one of PND and PNA. For in vivo studies, the composition can be fed to or injected into an animal model (e.g., a mouse) or administered to human subjects (including pregnant women) and its effects on incidence and severity of at least one of PND and PNA and associated conditions are then assessed. Based on the results, an appropriate dosage range and administration route can be determined.

Methods of calculating appropriate dose may depend on the nature of the active agent in the composition. For example, when the composition comprises live *L. rhamnosus* HN001, the dose may be calculated with reference to the number of live bacteria present. For example, as described herein the examples the dose may be established by reference to the number of colony forming units (cfu) to be administered per day. In examples where the composition comprises one or more *L. rhamnosus* HN001 derivatives, the dose may be calculated by reference to the amount or concentration of *L. rhamnosus* HN001 derivative present. For example, for a composition comprising *L. rhamnosus*

HN001 cell lysate, the dose may be calculated by reference to the concentration of *L. rhamnosus* HN001 cell lysate present in the composition.

By way of general example, the administration of from about $1 \times 10^6$ cfu to about $1 \times 10^{12}$ cfu of *L. rhamnosus* HN001 per kg body weight per day, preferably about $1 \times 10^6$ cfu to about $1 \times 10^{11}$ cfu/kg/day, about $1 \times 10^6$ cfu to about $1 \times 10^{10}$ cfu/kg/day, about $1 \times 10^6$ cfu to about $1 \times 10^9$ cfu/kg/day, about $1 \times 10^6$ cfu to about $1 \times 10^8$ cfu/kg/day, about $1 \times 10^6$ cfu to about $5 \times 10^7$ cfu/kg/day, or about $1 \times 10^6$ cfu to about $1 \times 10^7$ cfu/kg/day, is contemplated. Preferably, the administration of from about $5 \times 10^6$ cfu to about $5 \times 10^8$ cfu per kg body weight of *L. rhamnosus* HN001 per day, preferably about $5 \times 10^6$ cfu to about $4 \times 10^8$ cfu/kg/day, about $5 \times 10^6$ cfu to about $3 \times 10^8$ cfu/kg/day, about $5 \times 10^6$ cfu to about $2 \times 10^8$ cfu/kg/day, about $5 \times 10^6$ cfu to about $1 \times 10^8$ cfu/kg/day, about $5 \times 10^6$ cfu to about $9 \times 10^7$ cfu/kg/day, about $5 \times 10^6$ cfu to about $8 \times$cfu/kg/day, about $5 \times 10^6$ cfu to about $7 \times 10^7$ cfu/kg/day, about $5 \times 10^6$ cfu to about $6 \times$cfu/kg/day, about $5 \times 10^6$ cfu to about $5 \times 10^7$ cfu/kg/day, about $5 \times 10^6$ cfu to about $4 \times$cfu/kg/day, about $5 \times 10^6$ cfu to about $3 \times 10^7$ cfu/kg/day, about $5 \times 10^6$ cfu to about $2 \times 10^7$ cfu/kg/day, or about $5 \times 10^6$ cfu to about $1 \times 10^7$ cfu/kg/day, is contemplated.

In certain embodiments, periodic dose need not vary with body weight or other characteristics of the subject. In such examples, the administration of from about $1 \times 10^6$ cfu to about $1 \times 10^{13}$ cfu of *L. rhamnosus* HN001 per day, preferably about $1 \times 10^6$ cfu to about $1 \times 10^{12}$ cfu/day, about $1 \times 10^6$ cfu to about $1 \times 10^{11}$ cfu/day, about $1 \times 10^6$ cfu to about $1 \times 10^{10}$ cfu/day, about $1 \times 10^6$ cfu to about $1 \times 10^9$ cfu/day, about $1 \times 10^6$ cfu to about $1 \times 10^8$ cfu/day, about $1 \times 10^6$ cfu to about $5 \times 10^7$ cfu/day, or about $1 \times 10^6$ cfu to about $1 \times 10^7$ cfu/day, is contemplated. Preferably, the administration of from about $5 \times 10^7$ cfu to about $5 \times 10^{10}$ cfu per kg body weight of *L. rhamnosus* HN001 per day, preferably about $5 \times 10^7$ cfu to about $4 \times 10^{10}$ cfu/day, about $5 \times 10^7$ cfu to about $3 \times 10^{10}$ cfu/day, about $5 \times 10^7$ cfu to about $2 \times 10^{10}$ cfu/day, about $5 \times 10^7$ cfu to about $1 \times 10^{10}$ cfu/day, about $5 \times 10^7$ cfu to about $9 \times 10^9$ cfu/day, about $5 \times 10^7$ cfu to about $8 \times 10^9$ cfu/day, about $5 \times 10^7$ cfu to about $7 \times 10^9$ cfu/day, about $5 \times 10^7$ cfu to about $6 \times 10^9$ cfu/day, about $5 \times 10^7$ cfu to about $5 \times 10^9$ cfu/day, about $5 \times 10^7$ cfu to about $4 \times 10^9$ cfu/day, about $5 \times 10^7$ cfu to about $3 \times 10^9$ cfu/day, about $5 \times 10^7$ cfu to about $2 \times 10^9$ cfu/day, or about $5 \times 10^7$ cfu to about $1 \times 10^9$ cfu/day, is contemplated.

For example, as presented herein in the examples, an efficacious dose of freeze-dried *L. rhamnosus* HN001 was determined to be $6 \times 10^9$ cfu per day.

It will be appreciated that the composition is preferably formulated so as to allow the administration of an efficacious dose of *L. rhamnosus* HN001 or one or more derivatives thereof. The dose of the composition administered, the period of administration, and the general administration regime may differ between subjects depending on such variables as the severity of symptoms of a subject, the type of disorder to be treated, the mode of administration chosen, and the age, sex and/or general health of a subject. Furthermore, as described above the appropriate dose may depend on the nature of the active agent in the composition and the manner of formulation. For example, when the composition comprises live *L. rhamnosus* HN001, the dose may be calculated with reference to the number of live bacteria present. For example, as described herein the examples the dose may be established by reference to the number of colony forming units (cfu) to be administered per day. In examples where the composition comprises one or more *L. rhamnosus* HN001 derivatives, the dose may be calculated by reference to the amount or concentration of *L. rhamnosus* HN001 derivative to be administered per day. For example, for a composition comprising *L. rhamnosus* HN001 cell lysate, the dose may be calculated by reference to the concentration of *L. rhamnosus* HN001 cell lysate present in the composition.

It will be appreciated that preferred compositions are formulated to provide an efficacious dose in a convenient form and amount. In certain embodiments, such as but not limited to those where periodic dose need not vary with body weight or other characteristics of the subject, the composition may formulated for unit dosage. It should be appreciated that administration may include a single daily dose or administration of a number of discrete divided doses as may be appropriate. For example, as presented herein in the examples, an efficacious dose of *L. rhamnosus* HN001 may be formulated into a capsule for oral administration.

However, by way of general example, the inventors contemplate administration of from about 1 mg to about 1000 mg per kg body weight of a composition useful herein per day, preferably about 50 to about 500 mg per kg per day, alternatively about 150 to about 410 mg/kg/day or about 110 to about 310 mg/kg/day. In one embodiment, the inventors contemplate administration of from about 0.05 mg to about 250 mg per kg body weight of a composition useful herein.

Examples of infant formula, follow-on formula, or growing-up formula are presented herein. Compositions such as these may be formulated so that the concentration of *L. rhamnosus* HN001 present in the composition is such that an efficacious dose can be prepared using a readily measurable amount of the composition. For example, in certain embodiments, such as for example where the composition is an infant formula, the *L. rhamnosus* HN001 is provided at a concentration sufficient to supply an efficacious dose in an amount of formula capable of being easily measured by a parent or caregiver when preparing the formula for administration, such as, for example, with a measured scoop or similar as are commonly provided with infant formulas. Exemplary non-limiting concentrations of *L. rhamnosus* HN001 for use in such compositions include from about $5 \times 10^5$ cfu per gram of formula to about $10^9$ cfu per gram of formula, or from about $10^6$ cfu per gram of formula to about $10^8$ cfu per gram of formula.

In one embodiment a composition useful herein comprises, consists essentially of, or consists of at least about 0.1, 0.2, 0.5, 1, 5, 10, 15, 20, 25, 30, 35, 40, 45, 50, 55, 60, 65, 70, 75, 80, 85, 90, 95, 99, 99.5, 99.8 or 99.9% by weight of *L. rhamnosus* HN001 or a derivative thereof and useful ranges may be selected between any of these foregoing values (for example, from about 0.1 to about 50%, from about 0.2 to about 50%, from about 0.5 to about 50%, from about 1 to about 50%, from about 5 to about 50%, from about 10 to about 50%, from about 15 to about 50%, from about 20 to about 50%, from about 25 to about 50%, from about 30 to about 50%, from about 35 to about 50%, from about 40 to about 50%, from about 45 to about 50%, from about 0.1 to about 60%, from about 0.2 to about 60%, from about 0.5 to about 60%, from about 1 to about 60%, from about 5 to about 60%, from about 10 to about 60%, from about 15 to about 60%, from about 20 to about 60%, from about 25 to about 60%, from about 30 to about 60%, from about 35 to about 60%, from about 40 to about 60%, from about 45 to about 60%, from about 0.1 to about 70%, from about 0.2 to about 70%, from about 0.5 to about 70%, from about 1 to about 70%, from about 5 to about 70%, from about 10 to about 70%, from about 15 to about 70%, from about 20 to about 70%, from about 25 to about 70%, from about 30 to about 70%, from about 35 to about 70%, from about 40 to about 70%, from about 45 to about 70%, from about 0.1 to about 80%, from about 0.2 to about 80%, from about 0.5 to about 80%, from about 1 to about 80%, from about 5 to about 80%, from about 10 to about 80%, from about 15 to about 80%, from about 20 to about 80%, from about 25 to about 80%, from about 30 to about 80%, from about 35 to about 80%, from about 40 to about 80%, from about 45 to about 80%, from about 0.1 to about 90%, from about 0.2 to about 90%, from about 0.5 to about 90%, from about 1 to about 90%, from about 5 to about 90%, from about 10 to about 90%, from about 15 to about 90%, from about 20 to about 90%, from about 25 to about 90%, from about 30 to about 90%, from about 35 to about 90%, from about 40 to about 90%, from about 45 to about 90%, from about 0.1 to about 99%, from about 0.2 to about 99%, from about 0.5 to about 99%, from about 1 to about 99%, from about 5 to about 99%, from about 10 to about 99%, from about 15 to about 99%, from about 20 to about 99%, from about 25 to about 99%, from about 30 to about 99%, from about 35 to about 99%, from about 40 to about 99%, and from about 45 to about 99%).

In one embodiment a composition useful herein comprises, consists essentially of, or consists of at least about 0.001, 0.01, 0.05, 0.1, 0.15, 0.2, 0.3, 0.4, 0.5, 1, 2, 3, 4, 5, 6, 7, 8, 9, 10, 11, 12, 13, 14, 15, 16, 17, 18 or 19 grams of *L. rhamnosus* HN001 or a derivative thereof and useful ranges may be selected between any of these foregoing values (for example, from about 0.01 to about 1 grams, about 0.01 to about 10 grams, about 0.01 to about 19 grams, from about 0.1 to about 1 grams, about 0.1 to about 10 grams, about 0.1 to about 19 grams, from about 1 to about 5 grams, about 1 to about 10 grams, about 1 to about 19 grams, about 5 to about 10 grams, and about 5 to about 19 grams).

In one embodiment a composition useful herein comprising *L. rhamnosus* HN001 or a derivative thereof additionally comprises about 0.1, 0.5, 1, 5, 10, 15, 20, 25, 30, 35, 40, 45, 50, 55, 60, 65, 70, 75, 80, 85, 90, 95, 97, 99, or 99.9% by weight of fresh whole milk or a milk derivative and useful ranges may be selected between any of these foregoing values (for example, from about 0.1 to about 50%, from about 0.2 to about 50%, from about 0.5 to about 50%, from about 1 to about 50%, from about 5 to about 50%, from about 10 to about 50%, from about 15 to about 50%, from about 20 to about 50%, from about 25 to about 50%, from about 30 to about 50%, from about 35 to about 50%, from about 40 to about 50%, and from about 45 to about 50%). The milk derivative is preferably selected from recombined, powdered or fresh skim milk, recombined or reconstituted whole or skim milk powder, skim milk concentrate, skim milk retentate, concentrated milk, ultrafiltered milk retentate, milk protein concentrate (MPC), milk protein isolate (MPI), calcium depleted milk protein concentrate (MPC), low fat milk, low fat milk protein concentrate (MPC), casein, caseinate, milk fat, cream, butter, ghee, anhydrous milk fat (AMF), buttermilk, butter serum, beta serum, hard milk fat fractions, soft milk fat fractions, sphingolipid fractions, milk fat globular membrane fractions, milk fat globular membrane lipid fractions, phospholipid fractions, complex lipid fractions, colostrum, a colostrum fraction, colostrum protein concentrate (CPC), colostrum whey, an immunoglobulin fraction from colostrum, whey (including sweet whey, lactic acid whey, mineral acid whey, or reconstituted whey powder), whey protein isolate (WPI), whey protein concentrate (WPC), a composition derived from any milk or colostrum processing stream, a composition derived from the retentate or permeate obtained by ultrafiltration or microfiltration of any milk or colostrum processing stream, a composition derived from the breakthrough or adsorbed fraction obtained by chromatographic (including but not limited to ion and gel permeation chromatography) separation of any milk or colostrum processing stream, extracts of any of these milk derivatives including extracts prepared by multistage fractionation, differential crystallisation, solvent fractionation, supercritical fractionation, near critical fractionation, distillation, centrifugal fractionation, or fractionation with a modifier (e.g. soaps or emulsifiers), hydrolysates of any of these derivatives, fractions of the hydrolysates, and any combination of any two or more of these derivatives, including combinations of hydrolysed and/or non-hydrolysed fractions. It should be understood that the source of these derivatives may be milk or colostrum or a combination thereof.

It will be apparent that the concentration of *L. rhamnosus* HN001 or one or more derivatives thereof in a composition formulated for administration may be less than that in a composition formulated for, for example, distribution or storage, and that the concentration of a composition formulated for storage and subsequent formulation into a composition suitable for administration must be adequate to allow said composition for administration to also be sufficiently concentrated so as to be able to be administered at a therapeutically efficacious dose.

The compositions useful herein may be used alone or in combination with one or more other therapeutic agents. The therapeutic agent may be a food, drink, food additive, drink additive, food component, drink component, dietary supplement, nutritional product, medical food, nutraceutical, medicament or pharmaceutical. The therapeutic agent may be a probiotic agent or a probiotic factor, and is preferably effective to treat, prevent or attenuate at least one of PND and PNA or one or more of the symptoms of at least one of PND and PNA, or one or more risk associated with, or sequelae of, at least one of PND and PNA.

When used in combination with another therapeutic agent, the administration of a composition useful herein and the other therapeutic agent may be simultaneous or sequential. Simultaneous administration includes the administration of a single dosage form that comprises all components or the administration of separate dosage forms at substantially the same time. Sequential administration includes administration according to different schedules, preferably so that there is an overlap in the periods during which the composition useful herein and other therapeutic agent are provided.

Suitable agents with which the compositions useful herein can be separately, simultaneously or sequentially administered include one or more probiotic agents, one or more prebiotic agents, one or more phospholipids, one or more gangliosides, other suitable agents known in the art, and combinations thereof. Useful prebiotics include galactooligosaccharides (GOS), short chain GOS, long chain GOS, fructooligosaccharides (FOS), human milk oligosaccharides (HMO), short chain FOS, long chain FOS, inulin, galactans, fructans, lactulose, and any mixture of any two or more thereof. Some prebiotics are reviewed by Boehm G and Moro G (Structural and Functional Aspects of Prebiotics Used in Infant Nutrition, J. Nutr. (2008) 138(9):1818S-1828S), incorporated herein by reference. Other useful agents may include dietary fibre such as a fully or partially insoluble or indigestible dietary fibre. Accordingly, in one embodiment *L. rhamnosus* HN001 or derivative thereof may be administered separately, simultaneously or sequentially with one or more agents selected from one or more probiotics, one or more prebiotics, one or more sources of dietary fibre, one or more galactooligosaccharides, one or more short chain galactooligosaccharides, one or more long chain galactooligosaccharides, one or more fructooligosaccharides, one or more short chain galactooligosaccharides, one or more long chain galactooligosaccharides, one or more human milk oligosaccharides, inulin, one or more galactans, one or more fructans, lactulose, or any mixture of any two or more thereof.

In one embodiment, a composition useful herein includes or is administered simultaneously or sequentially with milk components such as whey protein, whey protein fractions (including acidic or basic whey protein fractions or a combination thereof), glycomacropeptide, lactoferrin, iron-lactoferrin, a functional lactoferrin variant, a functional lactoferrin fragment, a vitamin D or calcium, or combinations thereof. Useful milk component-containing compositions include compositions such as a food, drink, food additive, drink additive, dietary supplement, nutritional product, medical food or nutraceutical. Milk fractions enriched for these components may also be employed. Useful lactoferrins, fragments and compositions are described in international patent applications WO 03/082921 and WO 2007/043900, both incorporated herein by reference in their entirety.

It should be understood that the additional therapeutic agents listed above (both food based and pharmaceutical agents) may also be employed in a method according to the invention where they are administered separately, simultaneously or sequentially with a composition useful herein.

In one embodiment a composition useful herein further comprises a pharmaceutically acceptable carrier. In another embodiment the composition is or is formulated as a food, drink, food additive, drink additive, dietary supplement, nutritional product, medical food, enteral feeding product, parenteral feeding product, meal replacement, cosmeceutical, nutraceutical, medicament, or pharmaceutical. In one embodiment the composition is in the form of a tablet, a caplet, a pill, a hard or soft capsule or a lozenge. In one embodiment the composition is in the form of a cachet, a powder, a dispensable powder, granules, a suspension, an elixir, a liquid, or any other form that can be added to food or drink, including for example water, milk or fruit juice. In one embodiment the composition further comprises one or more constituents (such as antioxidants) which prevent or reduce degradation of the composition during storage or after administration. These compositions may include any edible consumer product which is able to carry bacteria or bacterial derivatives, including heat-killed, pressure-killed, lysed, UV- or light-treated, irradiated, fractionated or otherwise killed or attenuated bacteria. Examples of suitable edible consumer products include aqueous products, baked goods, confectionary products including chocolate, gels, ice creams, reconstituted fruit products, snack bars, food bars, muesli bars, spreads, sauces, dips, dairy products including yoghurts and cheeses, drinks including dairy and non-dairy based drinks, milk, milk powders, sports supplements including dairy and non-dairy based sports supplements, fruit juice, food additives such as protein sprinkles, dietary supplement products including daily supplement tablets, weaning foods and yoghurts, and formulas such as infant formula, follow-on formula, or growing-up formula, in powder or liquid form. Suitable nutraceutical compositions useful herein may be provided in similar forms.

It will be appreciated that different compositions of the invention may be formulated with a view to administration to a particular subject group. For example, the formulation of a composition suitable to be administered to a pregnant mother (for example, for indirect administration to a foetal subject or to a breastfeeding neonatal, infant, or child subject) may differ to that of a composition to be directly administered to the subject. It should also be appreciated that the formulation of a composition to be administered prophylactically may differ to that of a composition formulated for administration once at least one of PND and PNA or one or more symptoms of at least one of PND and PNA is present.

In one embodiment the composition for prophylactic use may further comprise or the *L. rhamnosus* HN001 may be used in combination with a probiotic agent such as *Lactobacillus rhamnosus* GG, *Lactobacillus acidophilus* (for example, *Lactobacillus acidophilus* (LAVRI-A1), *Lactobacillus reuteri* (for example *Lactobacillus reuteri* ATCC 55730) or *Bifidobacteria lactis* (for example, *Bifidobacteria lactis* strain HN019 or *Bifidobacteria lactis* strain BB12) or a combination of any two or more thereof.

In one embodiment, compositions for prophylactic administration, and particularly prophylactic indirect administration, may further comprise or the *L. rhamnosus* HN001 may be used in combination with a probiotic agent such as *Lactobacillus rhamnosus* GG, *Lactobacillus acidophilus* (for example, *Lactobacillus acidophilus* (LAVRI-A1), *Lactobacillus reuteri* (for example *Lactobacillus reuteri* ATCC 55730) or *Bifidobacteria lactis* (for example, *Bifidobacteria lactis* strain HN019 or *Bifidobacteria lactis* strain BB12) or a combination of any two or more thereof.

It will be appreciated that the term "prophylactic" and grammatical equivalents as used herein contemplates treatment, use, administration and the like before at least one of PND and PNA or the symptoms of at least one of PND and PNA are apparent.

In embodiments for use in the treatment of a subject having at least one of PND and PNA, or one or more symptoms of at least one of PND and PNA, the composition may further comprise or the *L. rhamnosus* HN001 may be combination with a probiotic agent such as *Lactobacillus rhamnosus* GG, *Lactobacillus acidophilus* (for example, *Lactobacillus acidophilus* (LAVRI-A1), *Lactobacillus reuteri* (for example *Lactobacillus reuteri* ATCC 55730) or *Bifidobacteria lactis* (for example, *Bifidobacteria lactis* strain HN019 or *Bifidobacteria lactis* strain BB12) or a combination of any two or more thereof.

As used herein, the term "therapeutic" and grammatical equivalents contemplate treatment, uses or administration where at least one of PND and PNA or the symptoms thereof are present.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

3 Postnatal Depression (PND)

Postnatal depression (PND), also called postpartum depression (PPD), is a type of clinical depression which can affect mothers (and fathers) after childbirth. While many women experience self-limited, mild symptoms postpartum, postnatal depression should be suspected when symptoms are severe and have lasted over two weeks.

Onset and Duration

PND usually begins between two weeks to a month after delivery, and may last several months or even a year.

Symptoms

Symptoms of PND in mothers may include: sadness, hopelessness, crying episodes, low self-esteem, irritability, guilt, a feeling of being overwhelmed, changes in sleeping patterns, changes in eating patterns, inability to be comforted, exhaustion, emptiness, inability to experience pleasure from activities usually found enjoyable, social withdrawal, low or no energy, becoming easily frustrated, feeling inadequate in taking care of the baby, decreased sex drive, occasional or frequent anxiety, interference with normal maternal-infant bonding.

Adverse Outcomes for Infants

PND can also lead to adverse outcomes for the child. The child may suffer from interference with normal maternal-infant bonding. PND may lead mothers to be inconsistent with childcare. Children of mothers with PND have been found to have higher rates of emotional problems, behavioural problems, psychiatric diagnoses (such as oppositional defiant disorder and conduct disorder), and hyperactivity.

Causes

The cause of PND is not well understood. Hormonal changes, genetics, and major life events have been hypothesized as potential causes. Evidence suggests that hormonal changes may play a role. Hormones which have been studied include estrogen, progesterone, thyroid hormone, testosterone, corticotropin releasing hormone, and cortisol.

Risk Factors

Factors suggested to increase the risk of PND include: prenatal depression or anxiety, a personal or family history of depression, moderate to severe premenstrual symptoms, maternity blues, birth-related psychological trauma, birth-related physical trauma, previous stillbirth or miscarriage, formula-feeding rather than breast-feeding, cigarette smoking, low self-esteem, childcare or life stress, low social support, poor marital relationship or single marital status, low socioeconomic status, infant temperament problems and colic.

4 Postnatal Anxiety (PNA)

It is also very common to experience postnatal anxiety and postnatal depression at the same time. In fact, in up to 50% of cases these two conditions co-occur.

Onset and Duration

Like PND, PNA usually begins between two weeks to a month after delivery, and may last several months or even a year.

Maternal symptoms of postnatal anxiety include: feelings of fear and worry which begin to dominate thinking, feeling irritable, feeling restless, feeling tense, feeling 'on edge', racing heart/strong palpitations, panic attacks, reoccurring worrying thoughts, feeling out of control, feeling that you are not doing things right, feeling that something terrible will happen, insomnia, avoiding situations for fear something bad will happen.

Postnatal anxiety can encompass, generalised anxiety disorder (GAD), obsessive compulsive disorder (OCD), Panic disorder, social phobia, specific phobia, and post-traumatic stress disorder (PTSD)—e.g. associated with a traumatic delivery.

Various aspects of the invention will now be illustrated in non-limiting ways by reference to the following examples.

Example

The aim of this study was to evaluate the effect of *Lactobacillus rhamnosus* HN001 given in pregnancy and postpartum on symptoms of maternal depression and anxiety in the postpartum period.

Materials and Methods

Pregnant women in Auckland and Wellington, NZ, were recruited to the study via health professionals and study information placed in pregnancy packs. Women were considered eligible if they were less than 16 weeks gestation, English-speaking, intending to breastfeed and if either they or the unborn child's biological father had a history of asthma, hayfever or eczema requiring medication. Women were excluded from the study if aged less than 16 years, planning to move outside the study centres during study duration, had a history of immunological disorders or medication, cardiac valve disease, required in-vitro fertilization, had major fetal abnormalities, were using probiotic drinks or supplements, participating in another randomized controlled trial (RCT), refused notification of their clinical carers, carried adrenaline for cows' milk allergy, had a history of a transplant or HIV, had used continuous antibiotic therapy for at least 3 months, miscarried between screening and enrolment, or were otherwise deemed unsuitable. Eligible women were enrolled into the study at 14-16 weeks gestation, where gestation was based on the earliest first trimester scan and, where this was not available, the date of the last menstrual period.

Study Design

Participating women were randomized to receive capsules containing either HN001 ($6 \times 10^9$ colony forming units (cfu)) or placebo (corn derived maltodextrin, identical in appearance and smell to the probiotic) to be taken daily from enrolment throughout pregnancy and up till six months post birth if still breastfeeding. HN001 powder was manufactured by Fonterra Co-operative Group Ltd using aseptic fermentation, concentration and freeze-drying, as previously described[8]. The placebo powder, corn-derived maltodextrin, was manufactured by Grain Processing Corp. Oregon, USA. Women were instructed to keep the capsules in the refrigerator and to avoid taking them within 10 minutes of consuming hot food or fluid.

Fonterra retained samples of capsules at 4° C. which were tested monthly to ensure viability of the contents over time. The viability of the contents of a selection of unused capsules returned from the field was tested three monthly. Loss in viability was less than 0.1 log, and within the limit of uncertainty of the counting method.

Randomization of capsules was performed by a statistician at Fonterra who had no contact with study investigators or participants. Randomization was stratified by study centre and performed in blocks of 20 according to a computer-generated randomization schedule and an allocation ratio of 1:1. Research staff screened and enrolled participants, providing eligible participants with the next available sequentially-numbered capsule container. All researchers, laboratory staff and participants were blind to study allocation.

Baseline information collected included age, ethnicity, parity, previous polycystic ovary syndrome (PCOS), body mass index (BMI) (weight (kg)/height (m)$^2$), waist circumference, antibiotic use during pregnancy but prior to enrolment and type 2 diabetes mellitus in the participant or a first degree relative. Among women with previous pregnancies greater than 20 weeks, we also collected a history of previous GDM and birth weight of previous babies.

Data Collection

Mothers were interviewed at baseline (14-16 weeks gestation) to collect information about maternal characteristics and demographics. When children were aged 6 months and 12 months old, mothers were visited and invited to complete a questionnaire about their psychological wellbeing thinking back to when their child was 1-2 months of age. If children were older than 12 months when the questionnaire was being used, mothers were posted the questionnaire or invited to complete it online via a secure link. Mothers and researchers remained blind to treatment assignation of participants at all follow up stages of the study.

Outcomes

Edinburgh Postnatal Depression Scale (EPDS): The EPDS is a 10 item screening questionnaire widely used to assess maternal mood (14). For the purposes of analysis, the standard cut-off of >12 was used to identify mothers at higher risk of postnatal depression.

State Trait Anxiety Inventory 6 item version (STAI6): The STAI6 is a short 6 item scale validated as an anxiety screening questionnaire based on the longer State Trait Anxiety Inventory (15). A cut-off of score >15 was used as an indicator of clinically significant levels of anxiety.

For both the EPDS and the STAI6 the questions were altered to use the past tense as mothers were asked to remember back to when their child was 1-2 months old and complete the questions based on how they were feeling at that time.

Infant Colic: Infant colic was assessed at the 6 month interview when mothers were asked if they had contacted a health professional because their child had colic at any time between birth and six months of age.

Sample Size and Statistical Analysis

With a sample size of 200 in each group and 13% drop-out rate the study had a 79% power to detect a 26% reduction in EPDS at the 5% level of significance.

Statistical analysis was conducted in SAS 9.4 using a generalised linear model for the continuous outcomes and logistic regression for categorical outcomes. Multivariable analysis of the relationship between probiotic supplementation and postnatal depression and anxiety scores, adjusted for the time since birth at which the questionnaires were completed and infant colic.

Ethics

The study received ethical approval from the New Zealand Multiregional Ethics Committee (MEC/11/09/77).

Results

Respondents

FIG. 1 shows the number eligible, recruited and allocated in the PIP Study. Of the 423 randomised women, 382 (90.3%) completed the psychological outcome measures. Of the 382 participants in this study, 11 completed the questionnaires at the 6 month infant visit, 112 completed them at the 12 month infant visit and the remaining 259 completed the measures online at a median child age of 2.1 years (IQR 1.8-2.4). A total of 195 of the women who responded were in the probiotic group and 187 were in the placebo group.

Depression and anxiety scores tended to increase with increasing interval between 1-2 months postpartum and when the questionnaire was completed (depression score increased by 0.85 per year, p=0.065; anxiety score increased by 0.66 per year, p=0.060). Infant colic was significantly associated with higher depression (multivariable p<0.0001) and anxiety (multivariable p<0.0001) scores, but was not significantly associated with probiotic supplementation group (p=0.456).

Probiotic Treatment and Psychological Outcomes

Table 1 shows the mean and standard deviation of depression and anxiety scores in the probiotic treatment and placebo groups. Mothers in the probiotic treatment group reported significantly lower depression scores (p=0.035) and anxiety scores (p=0.014) than those in the placebo group. After controlling for infant colic and time since birth that questionnaires were completed, probiotic supplementation remained significantly associated with reduced depression (p=0.037) and anxiety (p=0.014) scores.

TABLE 1

Depression and anxiety scores in the probiotic treatment and placebo groups

|  |  | Mean | Standard Deviation | Uni-variable P-value | Multi-variable P-value |
|---|---|---|---|---|---|
| Depression Scores* | | | | | |
| HN001 | N = 194 | 7.7 | 5.4 | 0.035 | 0.037 |
| Placebo | N = 187 | 9.0 | 6.0 | | |
| Anxiety Scores* | | | | | |
| HN001 | N = 192 | 12.0 | 4.0 | 0.014 | 0.014 |
| Placebo | N = 187 | 13.0 | 4.3 | | |

*Three participants had incomplete anxiety data on the STAI6 and one had incomplete depression data on the EPDS therefore scores could not be calculated.

Table 2 shows the number of women in the probiotic treatment and placebo groups who reported depression or anxiety scores above the cut-off point. The number of women reporting depression scores above the cut-off point did not differ significantly between the probiotic treatment and placebo groups (univariable p=0.086, multivariable p=0.106). However, women in the probiotic treatment group were significantly less likely to have anxiety scores above the cut-off point than the placebo group (p=0.001), this association remained statistically significant after controlling for infant colic and time since birth at questionnaire completion (p=0.002).

TABLE 2

Number and percentage of participants scoring at or above the cut-off point for depression and anxiety in the probiotic and placebo groups.

|  | HN001 N (%) | Placebo N (%) | Uni-variable P-value | Multi-variable P-Value |
|---|---|---|---|---|
| Depression Score* | | | | |
| Depressed | 32 (16.5) | 44 (23.5) | 0.086 | 0.106 |
| Not depressed | 162 (83.5) | 143 (76.5) | | |
| Anxiety Score* | | | | |
| Anxious | 30 (15.6) | 55 (29.4) | 0.001 | 0.002 |
| Not anxious | 162 (84.4) | 132 (70.6) | | |

*Three participants had incomplete anxiety data on the STAI6 and one had incomplete depression data on the EPDS therefore scores could not be calculated.

Discussion

This study demonstrated a significantly lower prevalence of symptoms of depression and anxiety postpartum in women supplemented with the probiotic HN001 during and after pregnancy than in those given a placebo. Furthermore, the number of women reporting clinically significant levels of anxiety on screening was significantly lower in the probiotic group. To our knowledge this is the first double-blind RCT of probiotics that has evaluated PND and anxiety.

In addition, our sample size was substantially larger than many previously reported RCTs of probiotics on mood and behaviour. In a systematic review of probiotic clinical trials, the median sample size of reviewed studies was 60 (12).

The finding that women supplemented with probiotics had fewer symptoms of postnatal anxiety and depression is consistent with two previous clinical studies of the effect of probiotics on mood in different populations. A RCT of 40 people with major depressive disorder treated with a combination of three probiotics or placebo also found a significant reduction in symptoms of depression on the Beck Depression Inventory (BDI) in the treatment group (16). A reduction in anxiety symptoms in a sample of 39 chronic fatigue patients randomised to receive *Lactobacillus casei* or placebo has also been reported, but the same study did not find a reduction of symptoms of depression on the BDI in the treatment group (17). Not all studies have demonstrated a significant positive effect of probiotic treatment on mood outcomes (12). The diversity of study populations, including those with schizophrenia (18), smokers (19) and irritable bowel syndrome patients (20), the range of probiotic strains used, small sample sizes and varying measures of mood make it difficult, if not impossible, to undertake any meta-analysis of these studies.

In our study infant colic was associated with higher depression and anxiety scores. There has been a suggestion in the literature that probiotic supplementation may benefit maternal mood by reducing infant colic. One study reported that direct probiotic supplementation of infants reduced infant colic and this in turn was associated with lower rates of maternal depression (21). While infants in our study are likely to have been exposed to some probiotic indirectly either in utero or via breastmilk they were not directly administered the probiotic, furthermore we found that infant colic did not differ between the probiotic and placebo groups and multivariable analysis showed that probiotic supplementation and absence of infant colic were independently associated with lower postnatal depression and anxiety scores.

The prevalence of depression and anxiety at 1-2 months post-partum in this study was higher than the 10% to 15% usually reported. This may be due to mothers in our study completing the questionnaire retrospectively. Possibly when mothers reflect back to how they felt 1 to 2 months after delivery, they realise how tiring caring for a newborn infant can be. In studies that survey prevalence of PND at an early time point, women may be less likely to rate themselves as depressed or anxious because they are expecting to feel exhausted.

In conclusion, this study provides evidence that probiotic supplementation with *L. rhamnosus* HN001 in pregnancy and postpartum reduces the prevalence of symptoms of PND and anxiety postpartum. Not all probiotic strains have the same effect on health and it is possible that the results found using *L. rhamnosus* HN001 are not generalisable to other probiotic strains. If replicated by other studies this probiotic may be useful for the prevention or treatment of depression and anxiety postpartum.

CONCLUSION

Mothers in this cohort who received the probiotic *L. rhamnosus* HN001 had significantly lower depression and anxiety scores in the postpartum period.

INDUSTRIAL APPLICABILITY

This invention relates to the use of probiotic bacteria, particularly *Lactobacillus rhamnosus* HN001 or derivatives thereof, and in particular in the treatment or prevention of at least one of PND and PNA. Methods for using the bacteria and compositions comprising the bacteria are also provided.

REFERENCES

1. Abbott M W, Williams M M (2006): Postnatal depressive symptoms among Pacific mothers in Auckland: prevalence and risk factors. *Aust N Z J Psychiatry* 40: 230-8.
2. PMMRC (2014): Eighth annual report of the Perinatal and Maternal Mortality Review Committee: Reporting mortality 2012. Wellington: Health Quality & Safety Commission.
3. Da Costa D, Dritsa M, Rippen N, Lowensteyn, & Khalife S (2006): Health-related quality of life in postpartum depressed women. *Arch Women's Ment Health* 9: 95-102.
4. Tronick E, Reck C (2009): Infants of depressed mothers. *Harvard Rev Psychiatry* 17:147-56.
5. Grace S L, Evindar A, & Stewart D E (2003): The effect of postpartum depression on child cognitive development and behavior: a review and critical analysis of the literature. *Arch Women's Ment Halth* 6: 263-274.
6. Battle C L, Salisbury A L, Schofield C A, Ortiz-Hernandez S (2013): Perinatal antidepressant use: understanding women's preferences and concerns *J Psychiatr Pract* 19: 443-53.
7. Dinan T G, Cryan J F (2016): Mood by microbes: towards clinical translation. *Genome Med* 6:36-38.
8. Collins S M, Kassam Z, Bercik P (2013): The adoptive transfer of behavioral phenotype via the intestinal microbiota: experimental evidence and clinical implications. *Curr Opin Microbiol* 16: 240-5.
9. Bravo J A, Forsythe P, Chew M V, Escaravage E, Savignac H M, Dinan T G, et al. (2011): Ingestion of *Lactobacillus* strain regulates emotional behaviour and central GABA receptor expression in a mouse via the vagus nerve. *PNAS* 108: 16050-16059.
10. Desbonnet L, Garrett L, Clarke G, Kiely B, Cryan J F, Dinan T G (2010): Effect of the probiotic *Bifidobacterium Infantis* in the maternal separation model of depression. *Neuroscience* 170: 1179-1188.
11. Carabotti M, Scirocco A, Maselli M A, Severi C (2015): The gut-brain axis: interactions between enteric microbiota, central and enteric nervous systems. *Ann Gastroenterol* 28: 203-209.
12. Romijn A R, & Rucklidge, J J (2015): Systematic review of evidence to support the theory of psychobiotics. *Nutr Rev* 73: 675-693.
13. Barthow C, Wickens K, Stanley T, Mitchell E A, Maude R, Abels P, et al. (2016): The Probiotics in Pregnancy Study (PIP Study): rationale and design of a double-blind randomised controlled trial to improve maternal health during pregnancy and prevent infant eczema and allergy. *BMC Pregnancy Childbirth* 16:133.
14. Cox J L, Holden J M & Sagovsky R (1987): Detection of postnatal depression. Development of the 10-item Edinburgh Postnatal Depression Scale. *Br J Psychiatry* 150: 782-786.
15. Marteau T M Bekker H (1992): The development of a six-item short-form of the state scale of the Spielberger State-Trait Anxiety Inventory (STAI). *Br J Clin Psychol* 31: 301-6.
16. Akkasheh G, Kashani-Poor Z, Tajabadi-Ebrahimi M, Jafari P, Akbari H, Taghizadeh M, et al. (2016): Clinical and metabolic response to probiotic administration in patients with major depressive disorder: A randomized, double-blind, placebo-controlled trial. *Nutrition* 32: 315-320.
17. Rao A V, Bested A C, Beaulne T M, Katzman M A, Iorio C, Beradi J M, et al. (2009): A randomized, double-blind, placebo-controlled pilot study of a probiotic in emotional symptoms of chronic fatigue syndrome. *Gut Pathog.* 1: 1-6.
18. Dickerson F B, Stallings C, Origoni A, Katsafanas E, Savage C L, Schweinfurth L A, et al. (2014): Effects of probiotic supplementation on schizophrenia symptoms and association with gastrointestinal functioning: A randomised, placebo-controlled trial. *Prim Care* Companion CNS Disord 16. pii: PCC.13m01579.
19. Reale M, Boscolo P, Bellante V, Tarantelli C, Di Nicola M, Forcella L, et al. (2012): Daily intake of *Lactobacillus casei* Shirota increases natural killer cell activity in smokers. *Br J Nutr* 108: 308-314.
20. Dapoigny M, Piche T, Ducrote P, Lundard B, Cardot J, Bernalier-Donadille A (2012): Efficacy and safety profile of LCR35 complete freeze-dried culture in irritable bowel syndrome: a randomized double-blind study. *World J Gastroenterol* 18: 2067-2075.
21. Mi G, Zhao L, Qiao D, Kang W, Tang M, & Xu J (2015): Effectiveness of *Lactobacillus reuteri* in infantile colic and colicky induced maternal depression: A prospective single blind randomized trial. *Antonie van Leeuwenhoek* 107: 154-155.
22. Craig M, and Howard, L (2009) Postnatal depression, BMJ Clin Evid, Published online 2009 Jan. 26.

The invention claimed is:

1. A method of treating or reducing the risk of preventing at least one of postnatal depression (PND) and postnatal anxiety (PNA) in a human adult female subject in need thereof, the method comprising administration of an effective amount of *Lactobacillus rhamnosus* HN001, deposited at the Australian Government Analytical Laboratories (AGAL) on Aug. 18, 1997, under deposit number NM97/09514, to the subject.

2. The method of claim 1, wherein the method comprises administering a composition comprising the *L. rhamnosus* HN001 and a physiologically acceptable diluent, adjuvant, carrier or excipient.

3. The method of claim 1, wherein the method comprises administering a food composition comprising the *L. rhamnosus* HN001.

4. The method of claim 3, wherein the food composition is selected from cultured milk, yoghurt, cheese, milk drink and milk powder.

5. The method of claim 1, wherein the method comprises administering a pharmaceutical composition comprising the *L. rhamnosus* HN001 and a pharmaceutically acceptable diluent, adjuvant, carrier or excipient.

6. The method of claim 1, wherein the method comprises administering a composition comprising the *L. rhamnosus* HN001, wherein the composition is a maternal formula, a maternal supplement, or a dietetic product.

7. The method of claim 1, wherein the *L. rhamnosus* HN001 is in a reproductively viable form.

8. The method of claim 1, wherein the *L. rhamnosus* HN001 is killed, lysed, fractionated or attenuated.

9. The method of claim 1, wherein the subject has an increased risk of at least one of PND or PNA.

10. The method of claim 9, wherein one or more factors leading to the increased risk are selected from prenatal depression or anxiety, a personal or family history of depression, moderate to severe premenstrual symptoms, maternity blues, birth-related psychological trauma, birth-related physical trauma, previous stillbirth or miscarriage, formula-feeding rather than breast-feeding, cigarette smoking, low self-esteem, childcare or life stress, low social support, poor marital relationship or single marital status, low socioeconomic status, infant temperament problems and colic.

11. The method of claim 1, wherein the subject is pregnant and the L. rhamnosus HN001 is administered after the first trimester of pregnancy.

12. The method of claim 1, wherein the subject is pregnant and the L. rhamnosus HN001 is administered between 14 and 16 weeks gestation.

13. The method of claim 1, wherein the subject is pregnant and the L. rhamnosus HN001 is administered from 14 to 16 weeks gestation until delivery.

14. The method of claim 1, wherein the subject is pregnant and the L. rhamnosus HN001 is administered from 14 to 16 weeks gestation to 6 months post- partum.

15. The method of claim 1, wherein the method further comprises simultaneous or sequential administration of a prebiotic.

16. The method of claim 15, wherein the prebiotic comprises fructooligosaccharides, galactooligosaccharides, or human milk oligosaccharides, or a combination thereof.

17. The method of claim 1, wherein administration of the *L. rhamnosus* HN001 results in a score of less than 13 in the Edinburgh Postnatal Depression Scale (EPDS).

18. The method of claim 1, wherein administration of the *L. rhamnosus* HN001 results in a score of less than 15 in the Stategrait Anxiety Inventory, 6 item version (STAI-6).

19. The method of claim 1, wherein
the subject is pregnant,
the subject is pregnant and is 35 years or older,
the subject is pregnant and has a history of at least one of PND and PNA, or
the subject is pregnant, is 35 years or older, and has a history of at least one of PND and PNA.

20. A method of reducing one or more risks associated with, or sequelae, at least one of postnatal depression (PND) and postnatal anxiety (PNA) in a human fetal, neonatal, infant, or child subject in need thereof, the method comprising administration of an effective amount of Lactobacillus rhamnosus HN001, deposited at AGAL on Aug. 18, 1997 under deposit number NM97/09514 dated 18 Aug. 1997, to the mother of the human fetal, neonatal, infant, or child subject.

21. The method of claim 20, wherein
the subject is a fetal subject and the *L. rhamnosus* HN001 is administered to the subject's mother, or
the subject is a neonatal, infant, or child subject, and the *L. rhamnosus* HN001 is administered to the subject's mother.

22. The method of claim 20, wherein the one or more risks associated with, or sequelae of, at least one of PND and PNA in the fetal, neonatal, infant, or child subject are selected from higher rates of emotional problems, behavioural problems, psychiatric diagnoses, and hyperactivity.

* * * * *

UNITED STATES PATENT AND TRADEMARK OFFICE
CERTIFICATE OF CORRECTION

PATENT NO. : 11,439,674 B2
APPLICATION NO. : 16/617813
DATED : September 13, 2022
INVENTOR(S) : Rebecca Slykerman It is certified that error appears in the above-identified patent and that said Letters Patent is hereby corrected as shown below:

On the Title Page

Column 2, Line 2, item [56] under Other Publications, delete "Pospartum" and insert --Postpartum--.

Page 2, Column 2, Line 32, item [56] under Other Publications, delete "Imunol" and insert --Immunol--.

Page 2, Column 2, Line 35, item [56] under Other Publications, delete "Microbiotia" and insert --Microbiota--.

In the Specification

Column 3, Line 16, delete "PNA" and insert --PNA.--.

Column 7, Line 8, delete "Genebank" and insert --Genbank--.

Column 11, Line 39, delete "stablisers," and insert --stabilizers,--.

Column 13, Line 18, delete "8×cfu/kg/day," and insert --8×$10^7$ cfu/kg/day,--.

Column 13, Line 19, delete "6×cfu/kg/day," and insert --6×$10^7$ cfu/kg/day,--.

Column 13, Line 21, delete "4×cfu/kg/day," and insert --4×$10^7$ cfu/kg/day,--.

Column 19, Line 4, delete "alter" and insert --after--.

Column 20, Line 22, delete "carers," and insert --careers,--.

Column 24, Line 23, delete "Halth" and insert --Health--.

Signed and Sealed this
Seventeenth Day of January, 2023

Katherine Kelly Vidal
*Director of the United States Patent and Trademark Office*

CERTIFICATE OF CORRECTION (continued)
U.S. Pat. No. 11,439,674 B2

In the Claims

Column 25, Claim 1, Line 32, after "risk of", delete "preventing".

Column 26, Claim 18, Line 35, delete "Stategrait" and insert --State-Trait--.

Column 26, Claim 20, Line 48, after "NM97/09514", delete "dated 18 Aug. 1997".